United States Patent
Saito et al.

(10) Patent No.: US 9,390,855 B2
(45) Date of Patent: *Jul. 12, 2016

(54) MONOLITHIC CERAMIC CAPACITOR CONTAINING PEROVSKITE COMPOUND

(71) Applicant: Murata Manufacturing Co., Ltd., Nagaokakyo-shi, Kyoto-fu (JP)

(72) Inventors: Yoshito Saito, Nagaokakyo (JP); Jun Ikeda, Nagaokakyo (JP); Kazuhisa Uchida, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/582,260

(22) Filed: Dec. 24, 2014

(65) Prior Publication Data

US 2015/0187497 A1    Jul. 2, 2015

(30) Foreign Application Priority Data

Dec. 27, 2013  (JP) .................................. 2013-272165

(51) Int. Cl.
*H01G 4/12* (2006.01)
*H01G 4/30* (2006.01)
(Continued)

(52) U.S. Cl.
CPC ........... *H01G 4/1218* (2013.01); *H01G 4/0085* (2013.01); *H01G 4/1227* (2013.01); *H01G 4/30* (2013.01); *G01N 23/2252* (2013.01); *H01G 4/2325* (2013.01)

(58) Field of Classification Search
CPC ....... H01G 4/1227; H01G 4/248; H01G 4/30; H01G 4/12
See application file for complete search history.

(56) References Cited

U.S. PATENT DOCUMENTS

| 2007/0135295 | A1* | 6/2007 | Sasabayashi | ........ | C01G 23/006 501/138 |
| 2011/0110014 | A1* | 5/2011 | Hirata | ..................... | B32B 18/00 361/301.4 |

(Continued)

FOREIGN PATENT DOCUMENTS

| JP | 2001-15375 A | 1/2001 |
| JP | 2003-100544 A | 4/2003 |

(Continued)

OTHER PUBLICATIONS

Official Communication issued in corresponding Japanese Patent Application No. 2013-272165, mailed on Oct. 27, 2015.

(Continued)

*Primary Examiner* — David M Sinclair
(74) *Attorney, Agent, or Firm* — Keating & Bennett, LLP

(57) ABSTRACT

In a monolithic ceramic capacitor, ceramic layers defining inner layers are mainly composed of a perovskite compound containing Ba and Ti. A portion of an electrically effective section in the ceramic layers near a connecting portion between the inner electrodes and an outer electrode undergoes mapping analysis by an energy-dispersive method. In regions of the resulting mapping image, the regions extending from the interfaces between the inner electrodes and a corresponding one of the ceramic layers to positions about ⅓ of the thickness of the ceramic layer in the stacking direction, ((L2−L3)/L1)×100≥50 is satisfied, where L1 represents the total length of grain boundaries, L2 represents the total length of grain boundaries where a rare-earth element is present, and L3 represents the total length of portions where the grain boundaries where the rare-earth element is present are overlapped with grain boundaries with a specific element present.

25 Claims, 3 Drawing Sheets

(51) Int. Cl.
*H01G 4/008* (2006.01)
*G01N 23/225* (2006.01)
*H01G 4/232* (2006.01)

(56) References Cited

U.S. PATENT DOCUMENTS

| | | | |
|---|---|---|---|
| 2012/0140375 A1* | 6/2012 | Kim | H01B 1/22 361/301.4 |
| 2012/0140376 A1 | 6/2012 | Ishihara et al. | |
| 2012/0147518 A1* | 6/2012 | Matsuda | H01G 4/1227 361/301.4 |
| 2015/0187497 A1* | 7/2015 | Saito | H01G 4/1218 361/301.4 |

FOREIGN PATENT DOCUMENTS

| | | |
|---|---|---|
| JP | 2009249257 A * | 10/2009 |
| JP | 2013-98312 A | 5/2013 |
| WO | 2011/021464 A1 | 2/2011 |

OTHER PUBLICATIONS

Official Communication issued in corresponding Korean Patent Application No. 10-2014-0188341, mailed on Mar. 8, 2016.

* cited by examiner

MONOLITHIC CERAMIC CAPACITOR CONTAINING PEROVSKITE COMPOUND

BACKGROUND OF THE INVENTION

1. Field of the Invention

The present invention relates to a monolithic ceramic capacitor that achieves improved moisture resistance reliability.

2. Description of the Related Art

In recent years, monolithic ceramic capacitors have been used in harsher environments than before.

To achieve good temperature characteristics and lifetime characteristics, Japanese Unexamined Patent Application Publication No. 2003-100544 discloses a monolithic ceramic capacitor. The monolithic ceramic capacitor includes dielectric layers composed of a dielectric ceramic composition, inner electrodes configured to hold the dielectric layers, and outer electrodes electrically connected to the inner electrodes. The dielectric ceramic composition is formed of about two or more types of ceramic grains having different concentrations of a predetermined component element.

In the monolithic ceramic capacitor described in Japanese Unexamined Patent Application Publication No. 2003-100544, however, when a voltage is applied to the monolithic ceramic capacitor in a high-temperature and high-humidity environment, the insulation resistance (IR) is disadvantageously reduced.

SUMMARY OF THE INVENTION

Accordingly, preferred embodiments of the present invention provide a monolithic ceramic capacitor that achieves improved moisture resistance reliability.

According to a preferred embodiment of the present invention, a monolithic ceramic capacitor includes a ceramic body including a plurality of dielectric ceramic layers and a plurality of inner electrodes, the plurality of dielectric ceramic layers and the plurality of inner electrodes being alternately stacked on each other in a stacking direction; and outer electrodes arranged on external surfaces of the ceramic body, the outer electrodes being electrically connected to respective ones of the inner electrodes, in which each of the dielectric ceramic layers contains a perovskite compound defining a main component, the perovskite compound containing Ba and Ti, in which a portion of an electrically effective section of the dielectric ceramic layers sandwiched between the inner electrodes, the portion being located in an area at or near a connecting portion between the inner electrodes and a corresponding one of the outer electrodes, is observed with a FE-TEM/EDS analyzer (a field-emission scanning transmission electron microscope equipped with an energy-dispersive X-ray spectrometer) to obtain images, and in which in regions extending from interfaces between the inner electrodes and a corresponding one of the dielectric ceramic layers to positions about ⅓ of a thickness of the corresponding dielectric ceramic layer in the stacking direction, the following relationship is satisfied:

$$((L2-L3)/L1) \times 100 \geq 50$$

where L1 represents a total length of ceramic grain boundaries detected and calculated from a TEM transmission image; L2 represents a total length of grain boundaries where a rare-earth element is present, the grain boundaries being detected from a mapping image; and L3 represents a total length of portions where the grain boundaries where the rare-earth element is present are overlapped with grain boundaries where at least one of Mn, Mg, and Si is present, the grain boundaries being detected from the mapping image.

Here, a value A given by the relationship $((L2-L3)/L1) \times 100$ indicates a proportion (%) of a total length L2 of grain boundaries where a rare-earth element is present (excluding a total length L3 of portions where the "grain boundaries with a rare-earth element present" are overlapped with "grain boundaries where at least one of Mn, Mg, and Si is present") with respect to the total length L1 of the ceramic grain boundaries in the TEM transmission image and the mapping image.

The phrase "an electrically effective section of the dielectric ceramic layers" refers to a section of the dielectric ceramic layers where the electrostatic capacitance of the capacitor is effectively generated.

When a voltage is applied to a monolithic ceramic capacitor in a high-temperature and high-humidity environment, the insulation resistance (IR) is reduced. The reason for this is water penetrating into the capacitor is electrolyzed to produce $H^+$ ions and $OH^-$ ions. These ions move mainly in portions of the electrically effective section of the dielectric ceramic layers between the inner electrodes, the portions being located in an area at or near connecting portions between inner electrodes and outer electrodes, thus increasing leakage current.

According to a preferred embodiment of the present invention, the value A is as high as about 50% or more in regions of the electrically effective section of the dielectric ceramic layers in an area at or near the connecting portions between the inner electrodes and the outer electrodes, the regions extending from the interfaces between the inner electrodes and a corresponding one of the dielectric ceramic layers to positions about ⅓ of the thickness of the corresponding dielectric ceramic layer in the stacking direction. So, the transfer of $H^+$ ions and $OH^-$ ions is significantly reduced or prevented, thus preventing the reduction in IR.

In the monolithic ceramic capacitor according to a preferred embodiment of the present invention, the rare-earth element preferably contains one or more elements selected from Dy, Tb, Ho, Y, Er, Gd, and La.

In this case, the monolithic ceramic capacitor has better moisture resistance reliability.

According to various preferred embodiments of the present invention, it is possible to provide a monolithic ceramic capacitor that achieves improved moisture resistance reliability.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 3A is a TEM transmission image on which ceramic boundaries are marked, FIG. 3B is a TEM transmission image on which grain boundaries where a rare-earth element is present are marked, and FIG. 3C is a TEM transmission image on which portions where grain boundaries where a rare-earth element is present are overlapped with grain boundaries where at least one of Mn, Mg, and Si is present are marked.

DETAILED DESCRIPTION OF THE PREFERRED EMBODIMENTS

Figure 1:
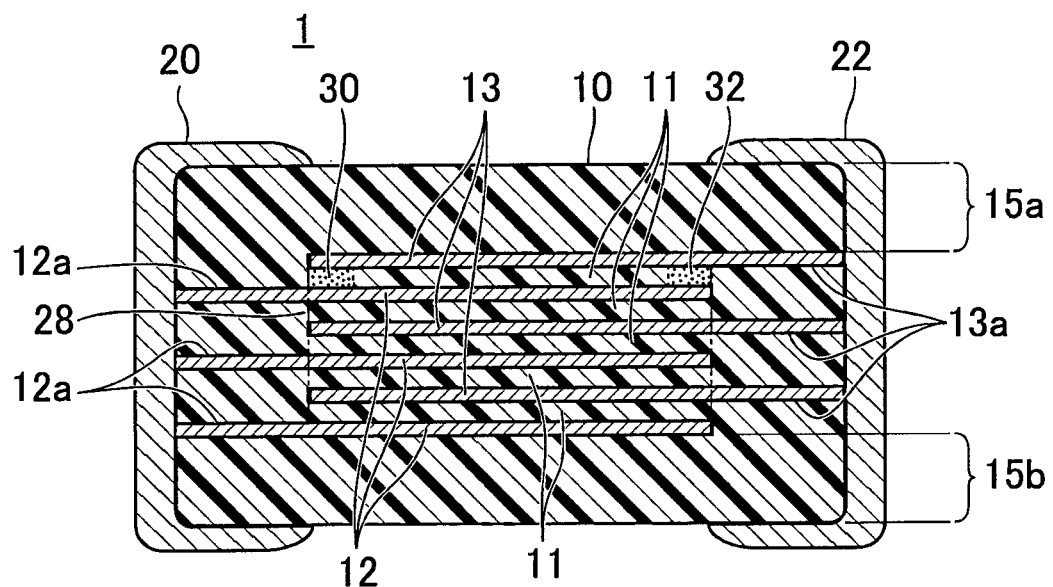
FIG. 1 is a vertical sectional view of a monolithic ceramic capacitor according to a preferred embodiment of the present invention.

FIG. 1 is a vertical sectional view of a monolithic ceramic capacitor 1. The monolithic ceramic capacitor 1 includes a ceramic body 10 and outer electrodes 20 and 22 arranged both right and left end portions of the ceramic body 10.

The ceramic body 10 includes a plurality of ceramic layers 11 defining inner layers, a plurality of inner electrodes 12 and 13 arranged at interfaces between the plurality of ceramic layers 11 defining inner layers, and ceramic layers 15a and 15b arranged vertically defining outer layers so as to sandwich the plurality of ceramic layers 11 defining inner layers. In other words, the ceramic body 10 preferably has a rectangular or substantially rectangular shape and a multilayer structure in which the ceramic layers 11, 15a, and 15b and the inner electrodes 12 and 13 are alternately stacked.

The ceramic layers 11 defining inner layers are preferably composed of a dielectric ceramic material that contains, as a main component, a perovskite compound containing Ba and Ti, such as barium titanate, for example. It is to be noted that the perovskite compound may have Ba partially substituted with at least one of Ca and Sr, and Ti partially substituted with Zr. The ceramic layers 11 defining inner layers preferably further contain auxiliary components, such as a Mg compound and a Mn compound, in addition to the main component, for example. Each of the ceramic layers 11 defining inner layers preferably has a thickness of about 0.3 µm to about 10.0 µm, more preferably about 0.3 µm to about 1.0 µm, and still more preferably about 0.3 µm to about 0.5 µm, for example. A smaller thickness of the ceramic layers defining inner layers results in a more uniform distribution of a rare-earth element in a desired region of the ceramic layers defining inner layers because heat is more instantaneously and uniformly conducted to the ceramic layers defining inner layers at the time of firing, thus providing a smaller monolithic ceramic capacitor having better reliability. When a rare-earth element added to a conductive paste defining inner layers is diffused into the ceramic layers defining inner layers at the time of firing, it is possible to efficiently diffuse the rare-earth element into a desired region in a shorter time.

The ceramic layers 15a and 15b vertically arranged to define outer layers are also preferably composed of the same dielectric ceramic material as the ceramic layers 11 defining inner layers. Note that the ceramic layers 15a and 15b defining outer layers may be composed of a different dielectric ceramic material from the ceramic layers 11 defining inner layers.

The inner electrodes 12 are opposite to the inner electrodes 13 in the thickness direction with the ceramic layers defining inner layers. Electrostatic capacitance is effectively generated in a portion where the inner electrodes 12 are opposite to the inner electrodes 13 with the ceramic layers 11 defining inner layers. That is, the phrase "the electrically effective section of the dielectric ceramic layers" indicates a section 28 of the ceramic layers 11 defining inner layers in the portion where the inner electrodes 12 are opposite to the inner electrodes 13 (a section of the ceramic layers 11 defining inner layers surrounded by a dot-and-dash line illustrated in FIG. 1).

Extending portions 12a of the inner electrodes 12 extend to the left end surface of the ceramic body 10 and are electrically connected to the outer electrode 20. Extending portions 13a of the inner electrodes 13 extend to the right end surface of the ceramic body 10 and are electrically connected to the outer electrode 22.

The inner electrodes 12 and 13 are preferably composed of, for example, Ni or a Ni alloy. Each of the inner electrodes 12 and 13 preferably has a thickness of about 0.3 µm to about 2.0 µm, more preferably about 0.3 µm to about 0.55 µm, and still more preferably about 0.3 µm to about 0.4 µm, for example.

The outer electrodes 20 and 22 are preferably composed of, for example, Ni, Cu, Ag, Pd, an Ag—Pd alloy, or Au. A Ni plating layer and a Sn plating layer are arranged on a surface of each of the outer electrodes 20 and 22.

In the monolithic ceramic capacitor 1 having the foregoing structure, a portion 30 (for example, a portion surrounded by a dotted line) in the electrically effective section 28 of the ceramic layers 11 defining inner layers between the inner electrodes 12 and 13, the portion 30 being located in an area at or near a connecting portion between the inner electrodes 12 and the outer electrode 20 and being closest to the extending portions 12a of the inner electrodes 12, is subjected to mapping analysis by known energy-dispersive X-ray spectroscopy (EDS). Alternatively, a portion 32 (for example, a portion surrounded by a dotted line) located in an area at or near a connecting portion between the inner electrodes 13 and the outer electrode 22 and being closest to the extending portions 13a of the inner electrodes 13, is subjected to mapping analysis by EDS.

The reason the portion 30 in an area at or near the connecting portions between the inner electrodes 12 and the outer electrode 20 (or the portion 32 in an area at or near the connecting portions between the inner electrodes 13 and the outer electrode 22) is preferably used as a portion measured by the mapping analysis is that water is liable to penetrate to this portion.

Figure 2:
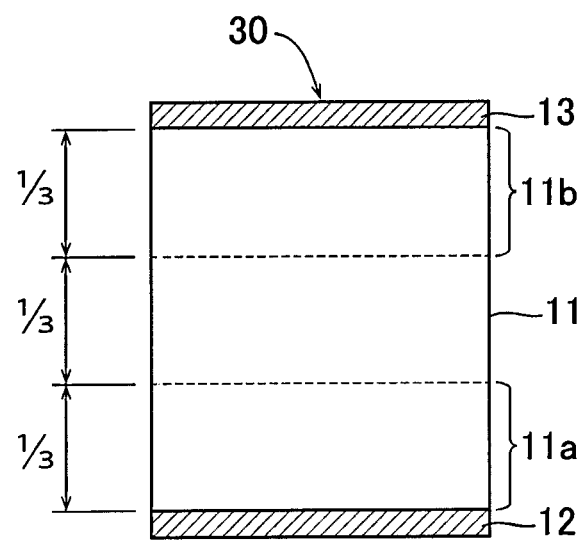
FIG. 2 is a schematic view of a mapping image obtained by mapping analysis using energy-dispersive X-ray spectroscopy (EDS).

As illustrated in FIG. 2, in regions 11a and 11b of a transmission image and a mapping image obtained by transmission observation and mapping analysis, the regions 11a and 11b extending from the interface between the inner electrode 12 and the ceramic layer 11 for an inner layer and the interface between the inner electrode 13 and the ceramic layer 11 for an inner layer to positions about ⅓ of the thickness of the ceramic layer 11 for an inner layer in the stacking direction, the following relationship is satisfied:

$$((L2-L3)/L1) \times 100 \geq 50$$

where L1 represents a total length of ceramic grain boundaries calculated from the TEM transmission image, L2 represents a total length of grain boundaries where a rare-earth element is present, the rare-earth element being detected from the mapping image, and L3 represents a total length of portions where the grain boundaries where the rare-earth element is present are overlapped with grain boundaries where an element other than Ba, Ca, Sr, Ti, Zr and O, which derive from the perovskite compound contained in the ceramic layers defining inner layers, and Ni, which derive from the inner electrodes, is present, the elements being detected from the mapping image.

FIG. 2 is a schematic view of a mapping image obtained by mapping analysis using energy-dispersive X-ray spectroscopy. In FIG. 2, the ceramic grain boundaries of the ceramic layers 11 defining inner layers are omitted.

In the monolithic ceramic capacitor 1, a value A given by the relationship $((L2-L3)/L1) \times 100$ preferably is as high as about 50% or more, for example, in the regions 11a and 11b of the portion 30 in the electrically effective section of the ceramic layers 11 defining inner layers, the portion 30 being located in an area at or near the connecting portions between the inner electrodes 12 and the outer electrode 20, and the regions 11a and 11b extending from the interface between the inner electrode 12 and the ceramic layer 11 for an inner layer and the interface between the inner electrode 13 and the ceramic layer 11 for an inner layer to positions about ⅓ of the thickness of the ceramic layer 11 for an inner layer in the stacking direction, for example. So, the transfer of $H^+$ ions and $OH^-$ ions is significantly reduced or prevented. That prevent the reduction in IR, thus resulting in the monolithic ceramic capacitor 1 having good moisture resistance reliability.

A non-limiting example of a method for producing the monolithic ceramic capacitor 1 will be described below.

(1) Preparation of Dielectric Raw-Material Mixture $BaTiO_3$ is weighed and wet-mixed with a ball mill to disintegrate aggregates. About 1.0 part by mole of $MgCO_3$, about 0.5 part by mole of $MnCO_3$, about 1.5 part by mole of $SiO_2$ are weighed as additive compounds with respect to about 100 parts by mole of Ti in $BaTiO_3$. $BaCO_3$ is appropriately weighed in such a manner that the ratio of the Ba content to the Ti content of $BaTiO_3$ after firing is about 1.007:1.

$BaTiO_3$ and these additive compounds are mixed together using a ball mill with water as a medium. The resulting mixture is subjected to evaporation and drying to give a dielectric raw-material mixture.

(2) Production of Ceramic Green Sheet

A polyvinyl butyral-based binder and an organic solvent, such as ethanol, are added to the dielectric raw-material mixture. The resulting mixture is wet-mixed using a ball mill to prepare a ceramic slurry. The ceramic slurry is formed into sheets by a lip process in such a manner that each of the sheets has a thickness of about 3.0 μm after firing. The resulting sheets are used as ceramic green sheets defining inner layers and ceramic green sheets defining outer layers.

(3) Formation of Inner Electrode

A conductive paste for inner electrodes, the conductive paste containing, for example, Ni or a Ni alloy defining a conductive component, is applied to the ceramic green sheets defining inner layers by, for example, screen printing to form the inner electrodes 12 and 13 having predetermined patterns. The conductive paste for inner electrodes contains a predetermined amount of a rare-earth element-containing compound (a rare-earth compound) defining an auxiliary component with respect to the main component, such as Ni. Examples of the rare-earth compound include $Y_2O_3$, $La_2O_3$, $Eu_2O_3$, $Gd_2O_3$, $Tb_4O_7$, $Dy_2O_3$, $Ho_2O_3$, $Er_2O_3$, and $Tm_2O_3$. The film thickness of each of the inner electrodes 12 and 13 is set so as to be about 1 μm after firing.

(4) Stacking of Layers

A predetermined number of the ceramic green sheets defining outer layers are stacked such that the thickness of the ceramic layers 15b defining outer layers is about 70 μm after firing. The ceramic green sheets defining inner layers on which the inner electrodes 12 and 13 are formed are stacked thereon in such a manner that the inner electrodes 12 and 13 are alternately stacked. A predetermined number of the ceramic green sheets defining outer layers are stacked thereon such that the thickness of the ceramic layers 15a defining outer layers is about 70 μm after firing. In this way, a mother ceramic body is produced.

The mother ceramic body is pressed in the stacking direction by a method, such as isostatic pressing. The mother ceramic body is cut into pieces each having a predetermined product size with a dicing saw, thus resulting in green ceramic bodies 10. In the width (W) direction of each of the green ceramic bodies 10, the gaps between side surfaces of each green ceramic body 10 and the inner electrodes 12 and 13 are about 100 μm. The corner portions and edge portions of the green ceramic bodies 10 are rounded by, for example, barrel polishing.

(5) Firing

The green ceramic bodies 10 are fired. Specifically, the green ceramic bodies 10 are heat-treated at a maximum temperature of about 270° C. in air or a stream of $N_2$ (in this preferred embodiment, in a stream of $N_2$). Subsequently, the green ceramic bodies 10 are heat-treated at a maximum temperature of about 700° C. in a stream of $N_2$—$H_2O$—$H_2$ at an oxygen partial pressure of about $10^{-10.6}$ MPa. The green ceramic bodies 10 are then fired at a maximum temperature of about 1300° C. in a stream of $N_2$ at an oxygen partial pressure of about $10^{-4.6}$ MPa and a predetermined rate of temperature increase. At the time of the firing, the green ceramic bodies 10 are cooled immediately after the temperature reaches a maximum temperature of about 1300° C. The firing temperature is preferably in the range of about 900° C. to about 1300° C. In this way, the ceramic green sheets defining inner layers are formed into the ceramic layers 11 defining inner layers. The ceramic green sheets defining outer layers are formed into the ceramic layers 15a and 15b defining outer layers.

In the firing process of the green ceramic body, the conductive component of the conductive paste for inner electrodes may diffuse into the ceramic layers defining inner layers.

(6) Formation of Outer Electrode

A conductive paste mainly containing Cu is applied to both end surfaces of each of the ceramic bodies 10 and baked at about 940° C. to form the outer electrodes 20 and 22. Furthermore, Ni—Sn plating layers are formed by wet plating on the surfaces of the outer electrodes 20 and 22. In this way, the monolithic ceramic capacitor 1 is produced. The dimensions of the monolithic ceramic capacitor 1 (including the outer electrodes 20 and 22) are about 2.0 mm long (L), about 1.25 mm wide (W), and about 0.5 mm high (T). Each of the ceramic layers 11 defining inner layers arranged between the inner electrodes 12 and 13 has a thickness of about 3.0 μm. The number of the ceramic layers 11 defining inner layers is about 100 layers.

3. Mapping Analysis by Energy-Dispersive X-Ray Spectroscopy

The mapping analysis of the monolithic ceramic capacitor 1 by energy-dispersive X-ray spectroscopy (EDS) will be described below.

(1) Preparation of Analytical Sample

The monolithic ceramic capacitor 1 is embedded in a resin. The vertical section (LT section) is ground in such a manner that the inner electrodes 12 and 13 are exposed.

In the monolithic ceramic capacitor 1, for example, the portion 30 in the electrically effective section 28 of the ceramic layers 11 defining inner layers, the portion 30 being located in an area at or near the connecting portions between the inner electrodes 12 and the outer electrode 20 and being closest to the extending portions 12a of the inner electrodes 12, is processed with a focused ion beam (FIB), thus providing a sample for observation with a scanning transmission electron microscope (TEM). The sample has a thickness of about 100 nm or less.

(2) Mapping Analysis by Energy-Dispersive X-Ray Spectroscopy

The sample is observed with a scanning transmission electron microscope (JEM-2200FS/JEM-2300T) equipped with a Schottky field-emission (FE) electron gun and subjected to mapping analysis by energy-dispersive X-ray spectroscopy. As a result, a scanning transmission electron microscope (TEM) image and a mapping image are obtained. The field of view of each of the images is set to a range such that a range about 1.3 times the average thickness of the ceramic layers 11 defining inner layers is observed in a direction perpendicular to the stacking direction and the entire ceramic layers 11 defining inner layers are observed in the stacking direction.

In this preferred embodiment, in order to accurately detect the distribution state of a small amount of an element added, the following conditions are satisfied:

(a) The observation time is about 10 hours.

(b) Electron-probe diameter is about 2 nm.

The sensitivity of the energy-dispersive X-ray spectroscopy is generally about 0.1 atm %. If an element has an intensity of less than about 0.5 atm %, the element is regarded as undetectable.

The total length L1 of ceramic boundaries, the total length L2 of grain boundaries where a rare-earth element is present, and the total length L3 of portions where the "grain boundaries where a rare-earth element is present" are overlapped with "grain boundaries where at least one of Mn, Mg, and Si is present" are calculated from the TEM transmission image and the mapping image with image analysis software. The calculation procedure is described below.

Figure 3A:
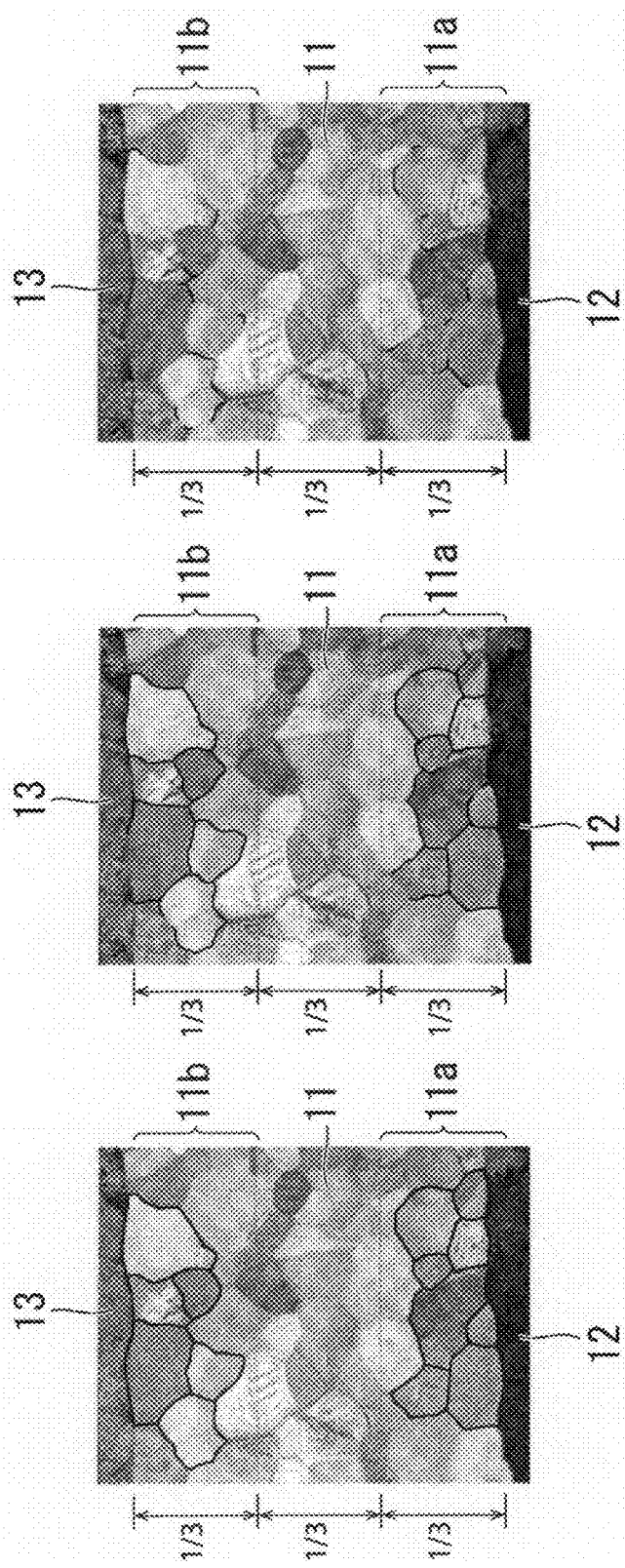
FIGS. 3A to 3C are TEM transmission images on which results from mapping analysis using EDS are marked.

(a) As illustrated in FIG. 3A, in the regions 11a and 11b extending from the interface between the inner electrode 12 and the ceramic layer 11 for an inner layer and the interface between the inner electrode 13 and the ceramic layer 11 for an inner layer to positions about ⅓ of the average thickness of the ceramic layers 11 defining inner layers in the stacking direction in the TEM transmission image, ceramic grain boundaries (boundaries of ceramic grains in which the whole of each of the grains is in the field of view of the mapping image and also include boundaries of ceramic grains in contact with the inner electrodes 12 and 13) are detected. The detected ceramic grain boundaries are marked with paint (black line portions in FIG. 3A). The total length L1 of the ceramic grain boundaries is measured and calculated with the image analysis software, such as, for example, a conventional software program referred to as "A-zou-kun Version 2.20" produced by Asahi Kasei Engineering Corp. (See, for example, http://www.asahi-kasei.co.jp/aec/business/sensing/product/azokun.html). The regions 11a and 11b are determined as follows: The thickness of the ceramic layer 11 for an inner layer in the stacking direction is measured in an area at or near both end portions of the ceramic layers 11 defining inner layers on the image. Points that trisect the thickness are determined in an area at or near the both end portions. Straight lines are drawn through the points. Regions extending from the interfaces between the inner electrodes and the ceramic layer 11 for an inner layer to the straight lines on the image are defined as the regions 11a and 11b.

Figure 3B:
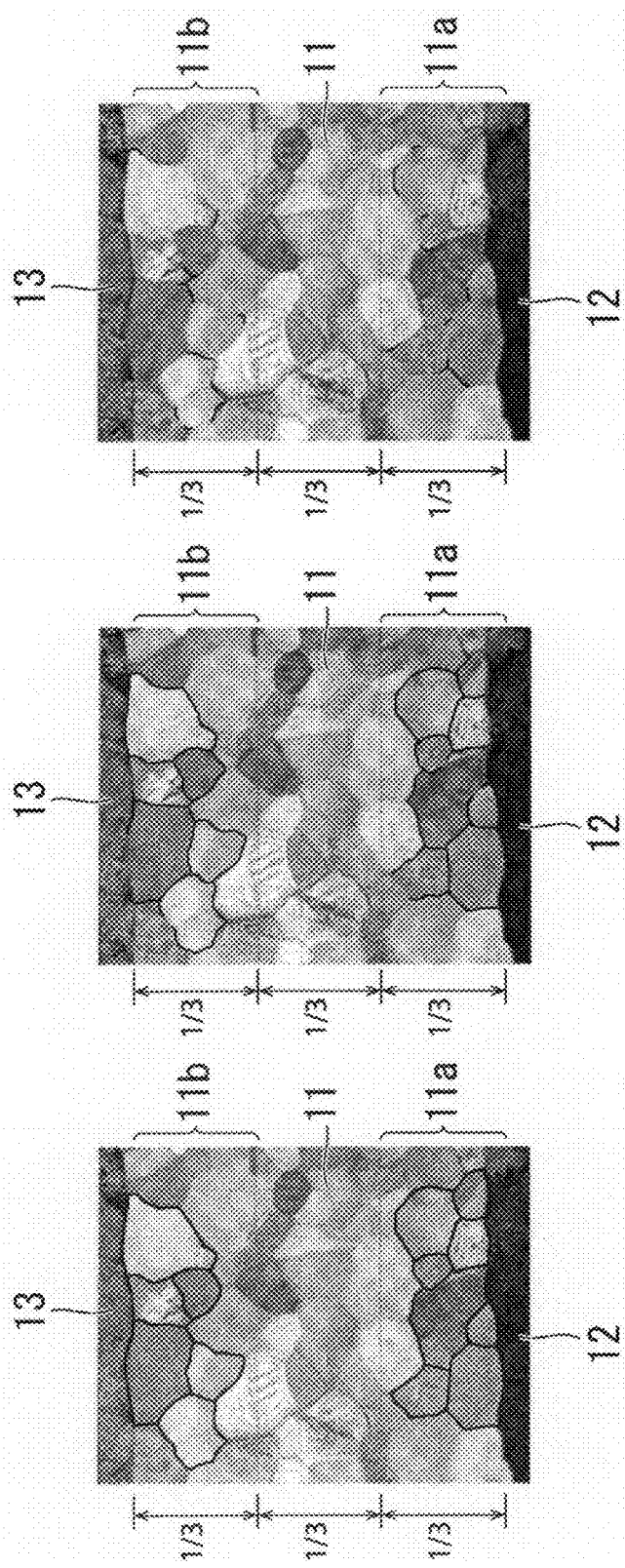

(b) As illustrated in FIG. 3B, grain boundaries where a rare-earth element is present are detected from the regions 11a and 11b of the TEM transmission image on which the results obtained by the mapping analysis are marked. The detected grain boundaries where the rare-earth element is present are marked with paint (black line portions in FIG. 3B). The total length L2 of the grain boundaries where the rare-earth element is present is measured and calculated with the image analysis software.

Figure 3C:
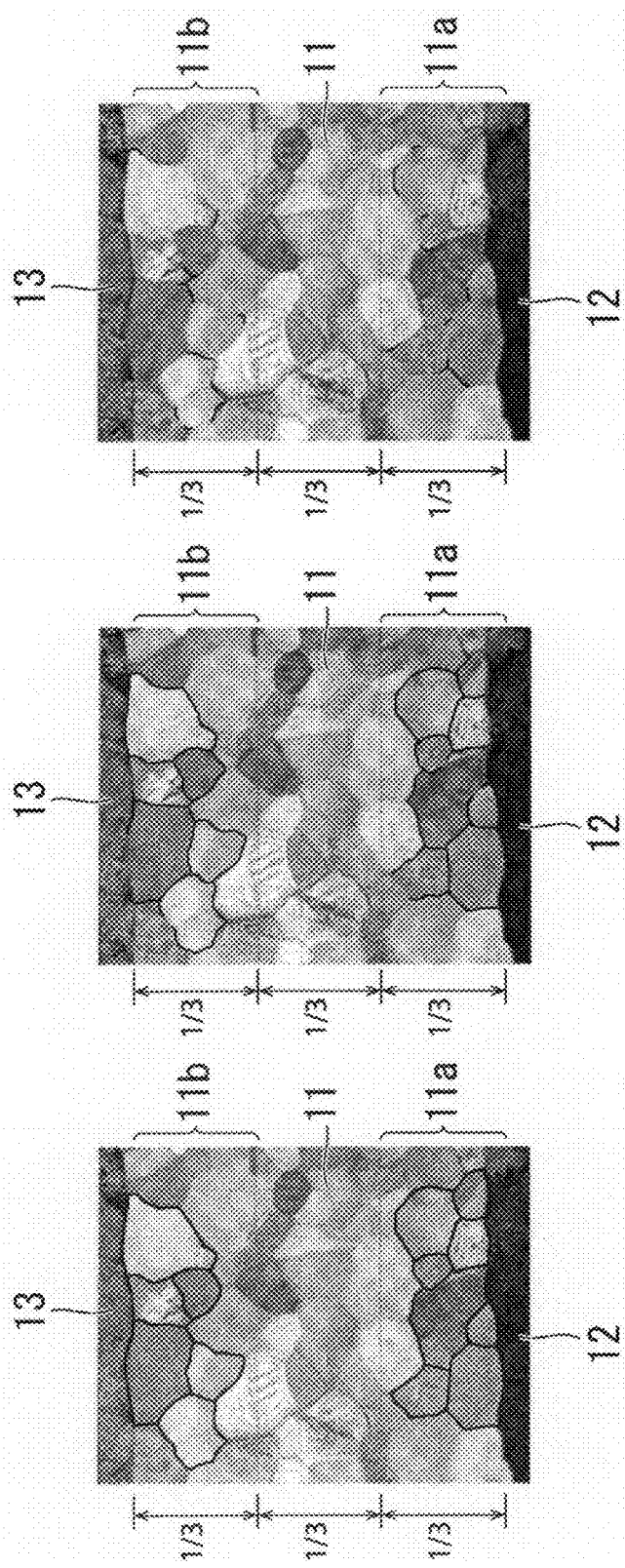

(c) As illustrated in FIG. 3C, portions where the "grain boundaries where the rare-earth element is present" are overlapped with the "grain boundaries where at least one of Mn, Mg, and Si is present" are detected from the regions 11a and 11b of the TEM transmission image on which the results obtained by the mapping analysis are marked. The detected portions are marked with paint (black line portions in FIG. 3C). The total length L3 of the portions is measured and calculated with the image analysis software.

(d) The value A is calculated from the total lengths L1, L2, and L3 determined in items (a) to (c).

$$A=((L2-L3)/L1)\times 100$$

In this way, the distribution state of the rare-earth element in the TEM transmission image is subjected to the mapping analysis in the regions 11a and 11b of the portion 30 in an area at or near the connecting portions between the inner electrodes 12 and the outer electrode 20, the regions 11a and 11b extending from the interface between the inner electrode 12 and the ceramic layer 11 for an inner layer and the interface between the inner electrode 13 and the ceramic layer 11 for an inner layer to the positions about ⅓ of the thickness of the ceramic layer 11 for an inner layer in the thickness direction.

Examples (1) Production of Analytical Sample

According to the foregoing production method, 17 types of the monolithic ceramic capacitors 1 defining analytical samples (sample Nos. 1 to 17, see Table 1) were produced.

Regarding a conductive paste for the inner electrodes, the conductive paste being used for the formation of the inner electrodes 12 and 13 of each of sample Nos. 1 to 17, a rare-earth compound defining an auxiliary component described in Table 1 is added to Ni, which defines a main component of Ni, in such a manner that a rare-earth element is added in an amount of about 0.68 parts by mole with respect to about 100 parts by mole of Ni in the conductive paste for the inner electrodes. For example, in the case of sample No. 1, the rare-earth compound is added in such a manner that about 0.68 parts by mole of Dy is added with respect to about 100 parts by mole of Ni in the conductive paste for the inner electrodes. In the case of sample No. 2, the rare-earth compound is added in such a manner that about 0.68 parts by mole of Tb is added with respect to about 100 parts by mole of Ni in the conductive paste for the inner electrodes.

In the case of the firing of the green ceramic body 10 of each of sample Nos. 1 to 16, the firing was performed at a maximum temperature of about 1300° C. in a stream of $N_2$ at a rate of temperature increase of about 40° C./sec and an oxygen partial pressure of about $10^{-4.6}$ MPa. At the time of the firing, the sample was cooled immediately after the temperature reached a maximum temperature of about 1300° C.

In the case of the firing of the green ceramic body 10 of sample No. 17, the firing was performed at a maximum temperature of about 1300° C. in a stream of $N_2$ at a rate of temperature increase of about 3.33° C./min and an oxygen partial pressure of about $10^{-4.6}$ MPa. At the time of the firing, after the temperature reached a maximum temperature of about 1300° C., the sample was maintained at a maximum temperature of about 1300° C. for about 2 hours and then cooled.

(2) Evaluation of Moisture Resistance Reliability of Analytical Sample

The moisture resistance reliability was evaluated as follows: the resulting monolithic ceramic capacitors 1 were allowed to stand for about 144 hours at a temperature of about 134.7° C., a relative humidity of about 95% RH, an applied voltage of about 10 V, and a gauge pressure of about 0.13 MPa. About 100 specimens were evaluated for each sample.

The defective fraction of the moisture resistance was defined as the proportion of the number of the specimens in which a reduction in IR occurred with respect to the number of the specimens evaluated. Here, the phrase "the specimens in which a reduction in IR occurred" indicates specimens in which the values of Log IR were reduced by about 0.5 or more with respect to the initial values.

Defective fraction of moisture resistance reliability=
(number of specimens in which reduction in IR occurred/number of specimens evaluated)×100 (%)

(3) Mapping Analysis of Analytical Sample by Energy-Dispersive X-Ray Spectroscopy Among the specimens of the monolithic ceramic capacitors 1 produced, about three specimens for each sample were subjected to the mapping analysis by the energy-dispersive X-ray spectroscopy.

The analysis was performed at about two positions for each specimen. Specifically, in the vertical section (LT section) of each of the monolithic ceramic capacitors 1, a middle portion of the monolithic ceramic capacitor 1 in the thickness direction T and a portion near the ceramic layers 15a (15b) defining outer layers were observed with a scanning transmission electron microscope (JEM-2200FS/JEM-2300T) to obtain mapping images.

The total lengths L1, L2, and L3 were measured and calculated with the image analysis software from the transmission images and the mapping images. Furthermore, the value A was calculated from the total lengths L1, L2, and L3. Table 1 describes the average value of the values measured at a total of about 12 positions (about three specimens×about two positions of the middle portion in the thickness direction T and the portion near the ceramic layers defining outer layers×about two positions of the regions 11a and 11b) for each sample.

(4) Evaluation Results

Figure 4:
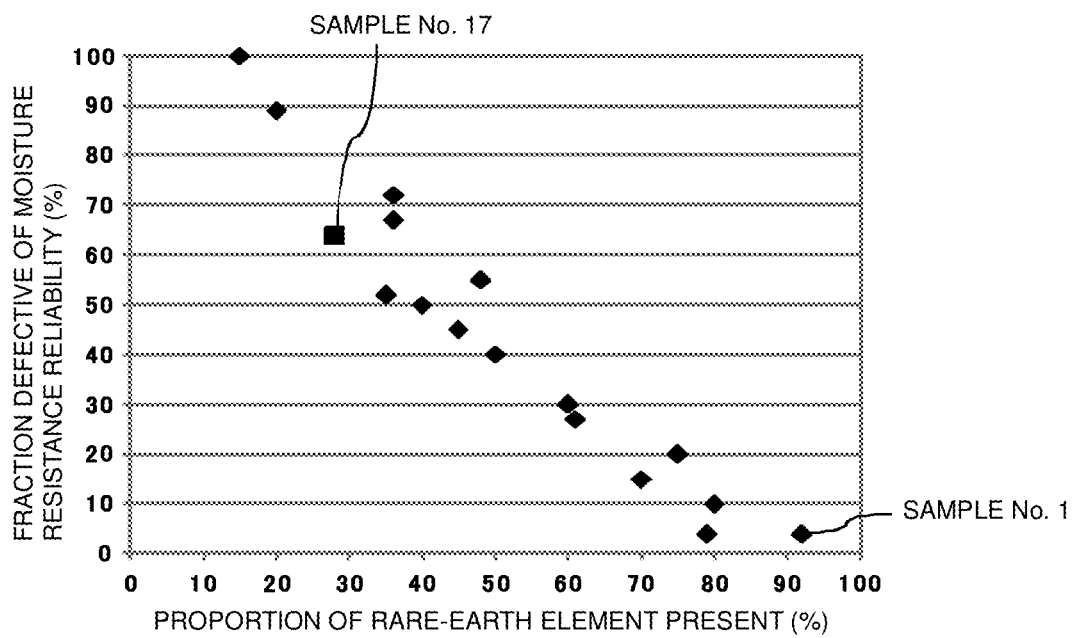
FIG. 4 is a graph illustrating the relationship between the value A and the defective fraction of the moisture resistance reliability.

Table 1 describes the evaluation results of the resulting monolithic ceramic capacitors 1. FIG. 4 illustrates the relationship between the value A and the defective fraction of the moisture resistance reliability.

TABLE 1

| Sample No. | Rare-earth compound | Value A [%] | Defective fraction [%] |
|---|---|---|---|
| 1 | $Dy_2O_3$ | 92 | 4 |
| 2 | $Tb_4O_7$ | 79 | 4 |
| 3 | $Ho_2O_3$ | 80 | 10 |
| 4 | $Y_2O_3$ | 70 | 15 |
| 5 | $Er_2O_3$ | 75 | 20 |
| 6 | $Gd_2O_3$ | 61 | 27 |
| 7 | $La_2O_3$ | 60 | 30 |
| 8 | $Tm_2O_3$ | 50 | 40 |
| 9 | $Eu_2O_3$ | 45 | 45 |
| 10 | $Yb_2O_3$ | 40 | 50 |
| 11 | $Sm_2O_3$ | 48 | 55 |
| 12 | $Lu_2O_3$ | 35 | 52 |
| 13 | $Nd_2O_3$ | 36 | 67 |
| 14 | $Pr_2O_3$ | 36 | 72 |
| 15 | $Ce_2O_3$ | 20 | 89 |
| 16 | $Sc_2O_3$ | 15 | 100 |
| 17 | $Dy_2O_3$ | 28 | 64 |

Table 1 demonstrates that for the Value A, a higher value of the value A has a tendency to lead to a lower defective fraction of the moisture resistance reliability in the regions 11a and 11b of the portion 30 (32) in the electrically effective section 28 of the ceramic layers 11 defining inner layers of each of the monolithic ceramic capacitors 1, the portion 30 (32) being located in an area at or near the connecting portions between the inner electrodes 12 (13) and the outer electrode 20 (22), and the regions 11a and 11b extending from the interface between the inner electrode 12 and the ceramic layer 11 for an inner layer and the interface between the inner electrode 13 and the ceramic layer 11 for an inner layer to the positions about ⅓ of the thickness of the ceramic layer 11 for an inner layer in the stacking direction.

To produce the capacitor having improved moisture resistance reliability (capacitor whose defective fraction of the moisture resistance reliability is about 40% or less), the value A preferably is about 50% or more, for example.

To produce the capacitor having better moisture resistance reliability (capacitor whose defective fraction of the moisture resistance reliability is about 30% or less), the value A preferably is about 60% or more, for example.

The results also demonstrated that for the capacitors of sample Nos. 1 and 17 (in which the conductive pastes for inner electrodes was used, the conductive pastes containing the same rare-earth element), the value A of the capacitor of sample No. 1 (the analytical sample produced at a rate of temperature increase of about 40° C./sec and a holding time of about zero hours at a maximum temperature of about 1300° C.) was higher than that of the capacitor of sample No. 17 (the analytical sample produced at a rate of temperature increase of about 3.33° C./min and a holding time of about 2 hours at a maximum temperature of about 1300° C.)

In the case where the rate of temperature increase was low, the rare-earth element diffuses throughout the ceramic layers defining inner layers and the ceramic layers 15a and 15b defining outer layers. Thus, the rare-earth element does not stay in the regions 11a and 11b extending from the interface between the inner electrode 12 and the ceramic layer 11 for an inner layer and the interface between the inner electrode 13 and the ceramic layer 11 for an inner layer to the positions about ⅓ of the thickness of the ceramic layer 11 for an inner layer in the stacking direction, thus reducing the value A in the regions 11a and 11b.

The present invention is not limited to the foregoing preferred embodiments. Various changes may be made without departing from the scope of the present invention.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:
1. A monolithic ceramic capacitor comprising:
   a ceramic body including:
      a plurality of dielectric ceramic layers; and
      a plurality of inner electrodes alternately stacked with the plurality of dielectric ceramic layers in a stacking direction; and
   outer electrodes arranged on external surfaces of the ceramic body and electrically connected to respective ones of the inner electrodes; wherein
   each of the dielectric ceramic layers contains, as its main component, a perovskite compound containing Ba and Ti and further contains at least one of Mn, Mg, and Si;
   a portion of an electrically effective section of the dielectric ceramic layers sandwiched between the inner electrodes is observed with a transmission electron microscope (TEM) and subjected to mapping analysis by energy-dispersive X-ray spectroscopy (EDS), the portion being located in an area at or near a connecting portion between the inner electrodes and a corresponding one of the outer electrodes; and in regions of a resulting mapping image obtained by the mapping analysis and a resulting TEM transmission image, the regions extending from interfaces between the inner electrodes and a corresponding one of the dielectric ceramic layers to positions about 1/3 of a thickness of a corresponding one of the dielectric ceramic layers in the stacking direction, a relationship ((L2−L3)/L1)×100≥50 is satisfied, where L1 represents a total length of ceramic grain boundaries detected from the TEM transmission image obtained by the TEM observation, L2 represents a total length of grain boundaries where a rare-earth element is present, the grain boundaries being detected from a mapping image obtained by the mapping analysis and the TEM transmission image; and L3 represents a total length of portions where the grain boundaries where the rare-earth element is present are overlapped with grain boundaries where at least one of Mn, Mg, and Si is present, the grain boundaries being detected from the mapping image obtained by the mapping analysis and the TEM transmission image.

2. The monolithic ceramic capacitor according to claim 1, wherein the rare-earth element contains one or more elements selected from Dy, Tb, Ho, Y, Er, Gd, and La.

3. The monolithic ceramic capacitor according to claim 1, wherein the ceramic layers defining inner layers include at least one of a Mg compound and a Mn compound.

4. The monolithic ceramic capacitor according to claim 1, wherein each of the ceramic layers defining inner layers has a thickness of about 0.3 μm to about 10.0 μm.

5. The monolithic ceramic capacitor according to claim 1, wherein each of the ceramic layers defining inner layers has a thickness of about 0.3 μm to about 1.0 μm.

6. The monolithic ceramic capacitor according to claim 1, wherein each of the ceramic layers defining inner layers has a thickness of about 0.3 μm to about 0.5 μm.

7. The monolithic ceramic capacitor according to claim 1, wherein the inner electrodes are made of one of Ni and a Ni alloy.

8. The monolithic ceramic capacitor according to claim 1, wherein each of the inner electrodes has a thickness of about 0.3 μm to about 2.0 μm.

9. The monolithic ceramic capacitor according to claim 1, wherein each of the inner electrodes has a thickness of about 0.3 μm to about 0.55 μm.

10. The monolithic ceramic capacitor according to claim 1, wherein each of the inner electrodes has a thickness of about 0.3 μm to about 0.4 μm.

11. The monolithic ceramic capacitor according to claim 1, wherein the outer electrodes are made of one of Ni, Cu, Ag, Pd, an Ag—Pd alloy, and Au.

12. The monolithic ceramic capacitor according to claim 1, wherein a Ni plating layer and a Sn plating layer are arranged on a surface of each of the outer electrodes.

13. The monolithic ceramic capacitor according to claim 1, wherein the monolithic ceramic capacitor has a length of about 2.0 mm, a width of about 1.25 mm, and a height of about 0.5 mm.

14. A monolithic ceramic capacitor comprising:
a ceramic body including:
a plurality of dielectric ceramic layers; and
a plurality of Ni-containing inner electrodes alternately stacked with the plurality of dielectric ceramic layers in a stacking direction; and outer electrodes arranged on external surfaces of the ceramic body and electrically connected to respective ones of the inner electrodes; wherein each of the dielectric ceramic layers contains, as its main component, a perovskite compound containing Ba and Ti and optionally containing Ca, Sr and Zr;

a portion of an electrically effective section of the dielectric ceramic layers sandwiched between the inner electrodes is observed with a transmission electron microscope (TEM) and subjected to mapping analysis by energy-dispersive X-ray spectroscopy (EDS), the portion being located in an area at or near a connecting portion between the inner electrodes and a corresponding one of the outer electrodes; and in regions of a resulting mapping image obtained by the mapping analysis and a resulting TEM transmission image, the regions extending from interfaces between the inner electrodes and a corresponding one of the dielectric ceramic layers to positions about 1/3 of a thickness of a corresponding one of the dielectric ceramic layers in the stacking direction, a relationship ((L2−L3)/L1)×100≥50 is satisfied, where L1 represents a total length of ceramic grain boundaries detected from the TEM transmission image obtained by the TEM observation, L2 represents a total length of grain boundaries where a rare-earth element is present, the grain boundaries being detected from a mapping image obtained by the mapping analysis and the TEM transmission image; and L3 represents a total length of portions where the grain boundaries where the rare-earth element is present are overlapped with grain boundaries where an element other than Ba, Ca, Sr, Ti, Zr, O and Ni is present, the grain boundaries being detected from the mapping image obtained by the mapping analysis and the TEM transmission image.

15. The monolithic ceramic capacitor according to claim 14, wherein the rare-earth element contains one or more elements selected from Dy, Tb, Ho, Y, Er, Gd, and La.

16. The monolithic ceramic capacitor according to claim 14, wherein the ceramic layers defining inner layers include at least one of a Mg compound and a Mn compound.

17. The monolithic ceramic capacitor according to claim 14, wherein each of the ceramic layers defining inner layers has a thickness of about 0.3 μm to about 10.0 μm.

18. The monolithic ceramic capacitor according to claim 14, wherein each of the ceramic layers defining inner layers has a thickness of about 0.3 μm to about 1.0 μm.

19. The monolithic ceramic capacitor according to claim 14, wherein each of the ceramic layers defining inner layers has a thickness of about 0.3 μm to about 0.5 μm.

20. The monolithic ceramic capacitor according to claim 14, wherein each of the inner electrodes has a thickness of about 0.3 μm to about 2.0 μm.

21. The monolithic ceramic capacitor according to claim 14, wherein each of the inner electrodes has a thickness of about 0.3 μm to about 0.55 μm.

22. The monolithic ceramic capacitor according to claim 14, wherein each of the inner electrodes has a thickness of about 0.3 μm to about 0.4 μm.

23. The monolithic ceramic capacitor according to claim 14, wherein the outer electrodes are made of one of Ni, Cu, Ag, Pd, an Ag—Pd alloy, and Au.

24. The monolithic ceramic capacitor according to claim 14, wherein a Ni plating layer and a Sn plating layer are arranged on a surface of each of the outer electrodes.

25. The monolithic ceramic capacitor according to claim 14, wherein the monolithic ceramic capacitor has a length of about 2.0 mm, a width of about 1.25 mm, and a height of about 0.5 mm.

* * * * *